US008834541B2

(12) United States Patent
Vargas Soto

(10) Patent No.: US 8,834,541 B2
(45) Date of Patent: Sep. 16, 2014

(54) BONE FIXATION ASSEMBLY

(76) Inventor: Héctor Anselmo Vargas Soto, Sabana Grande, PR (US)

(*) Notice: Subject to any disclaimer, the term of this patent is extended or adjusted under 35 U.S.C. 154(b) by 53 days.

(21) Appl. No.: 13/589,340

(22) Filed: Aug. 20, 2012

(65) Prior Publication Data

US 2014/0052195 A1     Feb. 20, 2014

(51) Int. Cl.
*A61B 17/04*     (2006.01)
*A61B 17/86*     (2006.01)
*A61F 2/08*     (2006.01)

(52) U.S. Cl.
USPC ............ 606/305; 606/264; 606/265; 606/300

(58) Field of Classification Search
USPC ................................. 606/264–275, 300–321
See application file for complete search history.

(56) References Cited

U.S. PATENT DOCUMENTS

| 8,048,124 | B2 | 11/2011 | Chin et al. |
| 8,097,025 | B2* | 1/2012 | Hawkes et al. ............... 606/269 |
| 2006/0241599 | A1* | 10/2006 | Konieczynski et al. ........ 606/61 |

* cited by examiner

*Primary Examiner* — Pedro Philogene
*Assistant Examiner* — Christina Negrellirodrigue
(74) *Attorney, Agent, or Firm* — Hoglund & Pamias, P.S.C.; Roberto J. Rios

(57) ABSTRACT

A bone fixation assembly comprises a tulip-shaped assembly and a bone fixation device such as a surgical or pedicle screw, comprising a head and a bone fixation portion. The tulip assembly comprises an upper portion to receive a rod and a lower portion that has a cavity in which the head of the bone fixation device rests. The cavity has an aperture below. The aperture has a length through which the tulip assembly may slide with respect to the bone fixation device, for movement of the tulip assembly when the bone fixation device is in place, while also maintaining the angular movement of the tulip assembly. The bone fixation device may comprise an aperture engaging part, which locks the bone fixation device position on the aperture length. A tulip assembly translation mechanism comprises a head, a cavity, an aperture to the cavity.

19 Claims, 16 Drawing Sheets

BONE FIXATION ASSEMBLY

STATEMENT REGARDING FEDERALLY SPONSORED RESEARCH AND DEVELOPMENT

N/A

RELATED APPLICATIONS

N/A

BACKGROUND

When the spinal column or when a bone or part of the skeletal system of a person is fractured, injured, or damaged, it may be beneficial to provide immobilization of that part of the body. Such immobilization, among other benefits, may provide support and stability, prevent further damage, and allow healing. One way to obtain such immobilization is with bone fixation systems or assemblies implanted through orthopedic surgery.

When a person is undergoing orthopedic surgery, often different screws are placed on different bones and parts of the body. The purpose of these screws is generally to provide fixation of a part of the body through the attachment of a rod or beam or other fixing device to a plurality of screws in bones of the body. The screws are generally inserted into the bone. For example, in a spinal column, the screws are inserted into the vertebral bodies or into the pedicles, as necessary. The rod is then attached to the screws. Because the screws are inserted into particular parts of the body, the inserted screws are not aligned in a straight line. This requires either the bending or curving of the rod or the attachment of additional parts to the screws, to the rod, or to both, for lateral or medial reaching.

Several bone fixation systems exist for providing stability and immobilization to the spinal column and to other parts of the body. It is desirable to develop devices and systems that allow for support of the rod without adding parts (such as screws, plates, and parts) to the implementation of the system, and without adding bulk to the sides of the spine or bone.

SUMMARY

A particular advantage of the present invention is that it allows for movement or translation of a tulip assembly after fixation of the screw or bone fixation device to a bone. In other words, the tulip assembly on top of the screw may be moved and repositioned in space. Some embodiments may also be configured for angular redirection of the tulip assembly, for fixation of the tulip assembly at a point of the aperture length, or for both.

In one exemplary embodiment, a bone fixation assembly comprises a bone fixation device and a tulip assembly. The bone fixation device comprises a bone fixation portion and a head, with the bone fixation portion extending away from the head. The tulip assembly comprises an upper portion and a lower portion, with the upper portion extending upward from the lower portion and structured to receive a rod. The lower portion comprises a cavity within the lower portion, and an aperture to the cavity, with the aperture located below the cavity, and the head being inside the cavity with the bone fixation portion extending out through the aperture. The aperture also comprises an aperture length and is dimensioned to prevent the entire bone fixation device from passing through the aperture and to allow the tulip assembly to slide on the bone fixation device through the aperture length.

Implementations of this aspect of the invention may include one or more of the following features. The bone fixation device may comprise a polyaxial screw; the polyaxial screw comprises the head and the bone fixation portion. The head may comprise a head height, a head width, and a head length, and the head length being longer than the head height and longer than the head width. The cavity may comprise an at least one spherical contour, with each of the at least one spherical contour extending upwards from the aperture. The head may comprise distal ends, wherein the distal ends reach the at least one spherical contour. Alternatively, the cavity may comprise an at least two spherical contours, each of the at least two spherical contours extending upwards from the aperture, and an at least one channel, each of the at least one channel extending between two of the at least two spherical contours while also extending upwards form the aperture through the aperture length and dimensioned to allow the head to pass through the at least one channel. The head may further comprise distal ends, with the distal ends distanced to reach inside each one of the at least two spherical contours. With such an apparatus, when the bone fixation device is fixed to a bone, then the tulip assembly may be moved with respect to the bone (or with respect to the bone fixation device) through the aperture length to reach the rod to be fitted in the tulip assembly.

In an alternative embodiment, a bone fixation assembly comprises a bone fixation device and a tulip assembly. The bone fixation device comprises a head and a bone fixation portion. The bone fixation portion comprises an aperture engaging portion, with the bone fixation portion extending away from the head. The tulip assembly comprises an upper portion and a lower portion, with the upper portion extending upward from the lower portion and structured to receive a rod. The lower portion comprises a cavity within the lower portion, and an aperture to the cavity, the aperture located below the cavity and the aperture comprising an aperture length, the aperture engaging portion structured to lock in position in the aperture length in at least in one orientation of the aperture engaging portion with respect to the aperture, the aperture dimensioned to prevent the entire bone fixation device from passing through the aperture and to allow the tulip assembly to slide on the bone fixation device through the aperture length when the aperture engaging portion is not locked in position with the aperture length.

Implementations of this aspect of the invention may include one or more of the following features. The bone fixation device may be a polyaxial screw; the polyaxial screw comprises the head and the bone fixation portion (which comprises the aperture engaging portion). The head may have a head height, a head width, and a head length, and the head length may be longer than the head height and longer than the head width. The aperture engaging portion may have an elliptic cylindrical shape. When the bone fixation device is fixed to a bone and the aperture engaging portion is not locked in position with respect to the aperture length, then the tulip assembly may be moved to reach the rod to be fitted in the tulip assembly and then the tulip assembly may be locked in position with respect to the aperture length.

In another aspect, the invention features a tulip assembly translation mechanism of a bone fixation assembly. The mechanism comprises a head of a bone fixation device, a cavity of a tulip assembly, and an aperture to the cavity. The head is located inside the cavity. The aperture comprises an aperture length and is located below the cavity. The aperture is dimensioned to prevent the head from passing through the aperture, and the cavity is dimensioned to allow the head to move through the cavity by the aperture length.

Implementations of this aspect of the invention may include one or more of the following features. The head may comprise a head height, a head width, and a head length, with the head length longer than the head height and longer than the head width. The mechanism may further comprise an aperture engaging part extending out through the aperture and structured to lock in position in the aperture length in at least one orientation of the aperture engaging part with respect to the aperture. The aperture engaging part may lock movement through the aperture length with the aperture through surface pressure between the aperture engaging part and the aperture in at least one orientation of the aperture engaging part with respect to the aperture. The aperture engaging part may have an elliptic cylindrical shape. The cavity may further comprise an at least one spherical contour, each of the at least one spherical contour extending upwards from the aperture. The head further comprises distal ends, wherein the distal ends reach the at least one spherical contour. Alternatively, the cavity further comprises an at least two spherical contours and an at least one channel. Each one of the at least two spherical contours is extending upwards from the aperture, and each of the at least one channel extending between two of the at least two spherical contours while also extending upwards form the aperture through the aperture length and dimensioned to allow the head to pass through the at least one channel. The head further comprises distal ends, with the distal ends distanced to reach each one spherical contour of the at least two spherical contours, whereby the head may be moved in different angles with respect to the cavity when the distal ends are contiguous to one spherical contour of the at least two spherical contours.

The invention itself, both as to its configuration and its mode of operation and its features, aspects, and advantages, will be best understood, and additional objects and advantages thereof will become apparent, by the following detailed description of a preferred embodiment taken in conjunction with the accompanying drawings and appended claims.

The Applicant hereby asserts, that the disclosure of the present application may include more than one invention, and, in the event that there is more than one invention, that these inventions may be patentable and non-obvious one with respect to the other.

Further, the purpose of the accompanying abstract is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE DRAWINGS

The accompanying drawings which are incorporated herein constitute part of the specifications and illustrate the preferred embodiments of the invention.

DESCRIPTION

Figure 1:
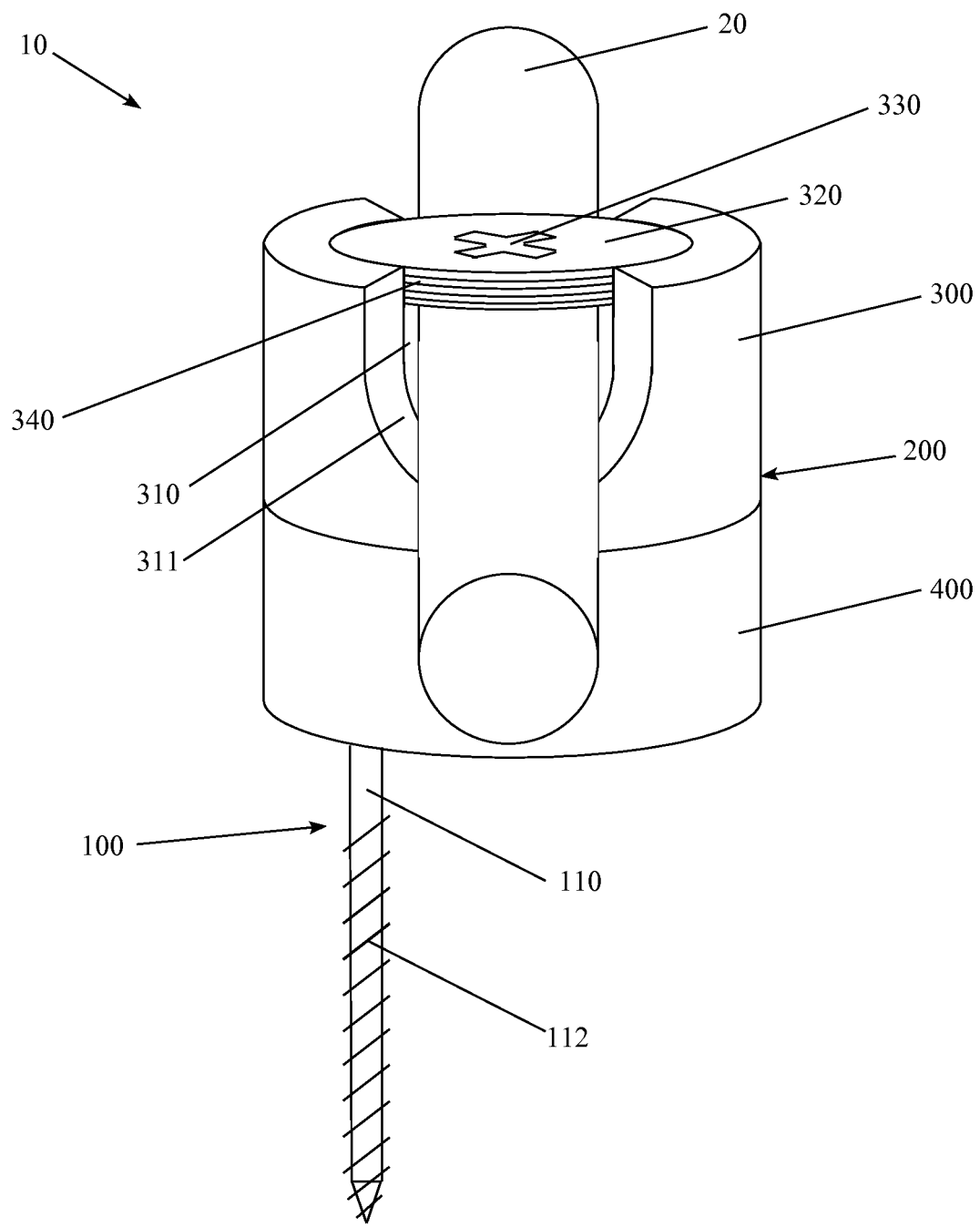
FIG. 1 is a perspective view showing the top of a bone fixation assembly with features of the invention, according to one exemplary embodiment.

FIG. 1 shows a bone fixation assembly 10 with a rod 20. Bone fixation assembly 10 has a bone fixation device 100 and a tulip assembly 200. The bone fixation device may be any device or article that attaches to bones or other structures; although it could be a device that wraps around a bone, a device that grows or bonds to tissue, or some other type of attaching device, generally this device will be a screw, as shown in FIG. 1. This screw or bone fixation device 100 comprises a head (not shown) and a bone fixation portion 110. The bone fixation portion 110 drives through bone and attaches to tissue with threads 112.

Tulip assembly 200 is on top of the bone fixation device 100. Tulip assembly 200 has an upper portion 300 which extends upward from the lower portion 400. To make apparent the division between upper portion 300 and lower portion 400, FIG. 1 provides a line has between such parts. The upper portion 300 has a rod channel 310 created by a u-shaped saddle 311, made by two concavities on the wall of upper portion 300, which is dimensioned to receive the rod 20. There are other means to receive a rod on a tulip assembly, which shall be apparent to a person skilled in the art. The rod 20 is secured by locking element 320. Locking element 320 in FIG. 1 is a washer-type locking part, with locking element threads 340 to secure locking element 320 to the upper portion 300, and driving element 330 to insert locking element 320 into the upper portion 300 with the appropriate driving tool. Notice that bone fixation device 100 is not centered with the tulip assembly 200.

Figure 2:
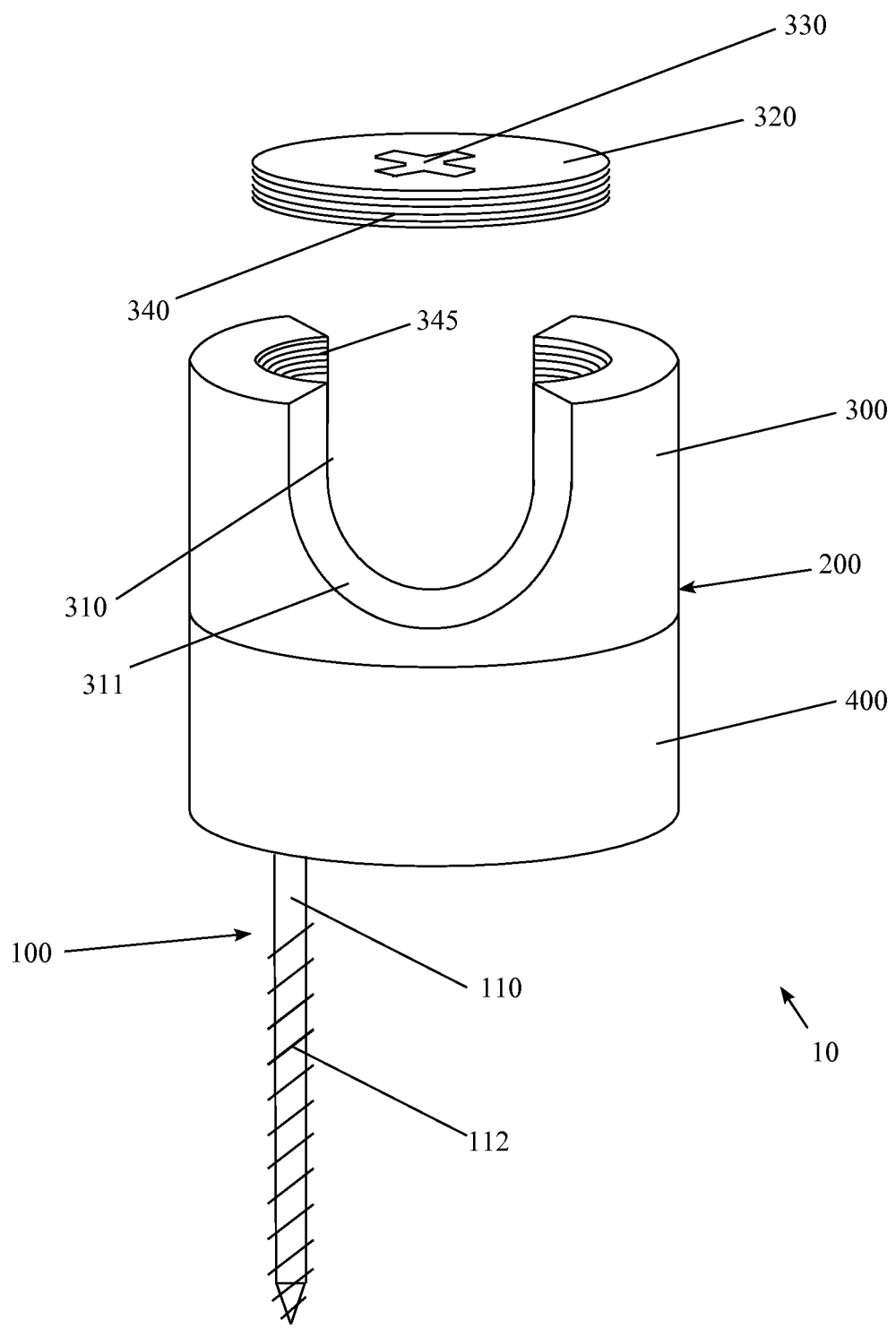
FIG. 2 is a perspective and partially exploded view showing the top of a bone fixation assembly with features of the invention, according to one exemplary embodiment, with a locking element separated from the bone fixation assembly.

FIG. 2 is the same as FIG. 1, but FIG. 2 does not show rod 20. Instead, FIG. 2 shows locking element 320 removed, floating above tulip assembly 200. With locking element 320 out of the way, FIG. 2 shows upper portion threads 345, which correspond to locking element threads 340 and enable the attachment of locking element 320 to upper portion 300.

Figure 3:
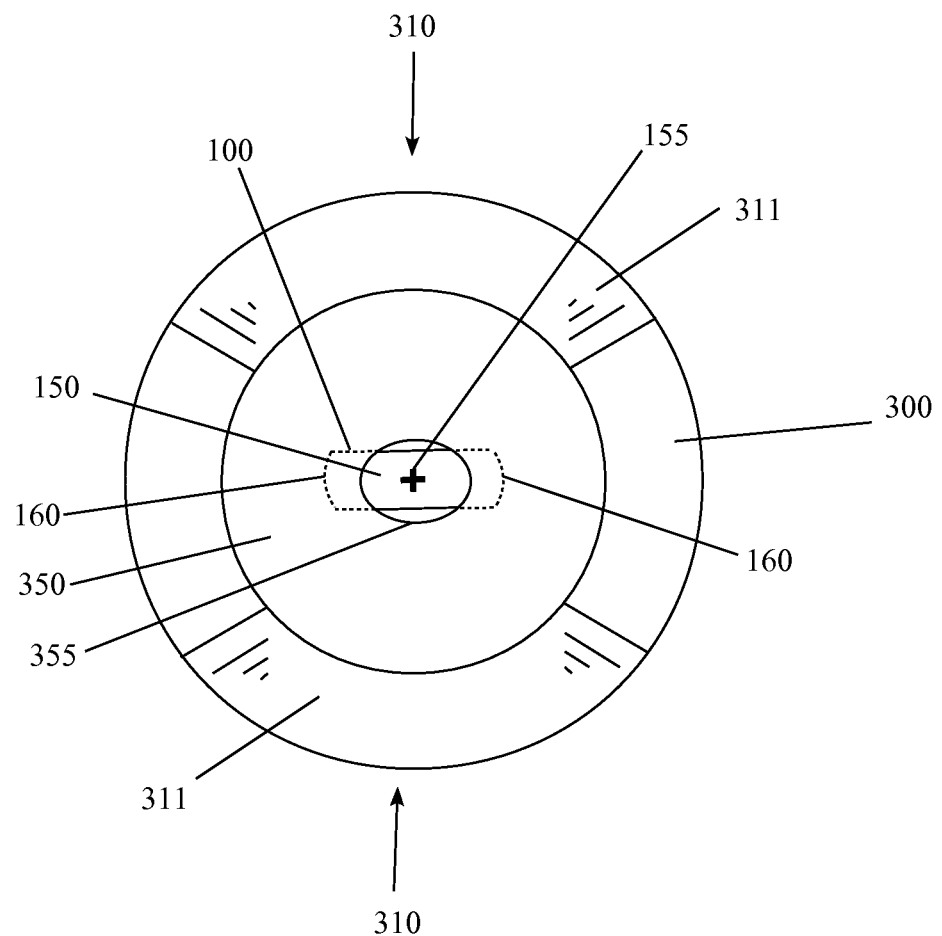
FIG. 3 is a partially transparent top view of a bone fixation assembly with features of the invention, according to one exemplary embodiment of the invention.

FIG. 3 is a top view of the embodiment shown in FIGS. 1 and 2, without the rod 20 and without the locking element 320. Only upper portion 300 is seen of the tulip assembly 200. The figure shows the top of saddle 311 and shows the direction of rod channel 310. On the center of the upper portion floor 350 is a driving hole 355. Below the driving hole 355 is driving shaft 455 (not shown). Through driving hole 355 can be seen the head 150 of the bone fixation device 100. The upper portion floor 350 (and the lower portion, not shown) is partially transparent for the viewer's benefit, showing the distal ends 160 of head 150. On top of head 150 is a head driving element 155. An appropriate driving tool may be inserted through the upper portion 300 and would go into driving hole 355 and grasps into the head driving element 155 to screw or place the bone fixation assembly 10 into a bone.

Figure 4:
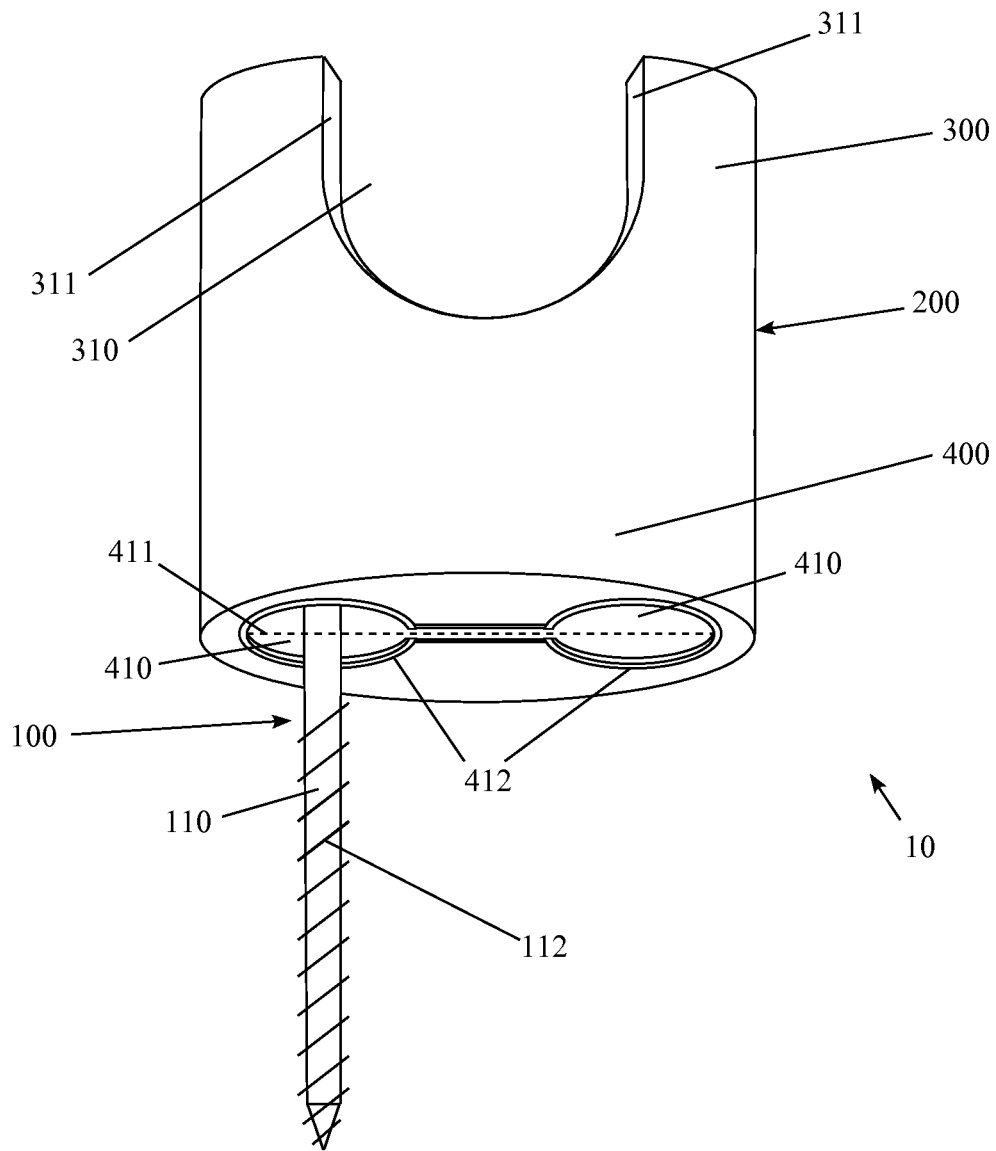
FIG. 4 is a perspective view showing the bottom of a bone fixation assembly with features of the invention, according to one exemplary embodiment.

FIG. 4 is a perspective view of one of the preferred embodiments of the invention, as also shown in FIGS. 1 through 3, but showing the bottom of tulip assembly 200. The line between upper portion 300 and lower portion 400 has been removed to make it apparent that there is no need to actually have a line there. An aperture 410 is at the bottom of the tulip assembly 200, below a cavity (not shown) inside lower portion 400. This aperture has an aperture length 411, which is a distance or path (or length) through which the bone fixation device 100 may be displaced. To be more exact, assuming the bone fixation device 100 is fixed in place (such as when inserted in a bone), the aperture length or distance 411 is the path through which the tulip assembly 200 may be moved when the tulip assembly 200 is sliding or translating on top of the fixed bone fixation device 100.

Figure 5:
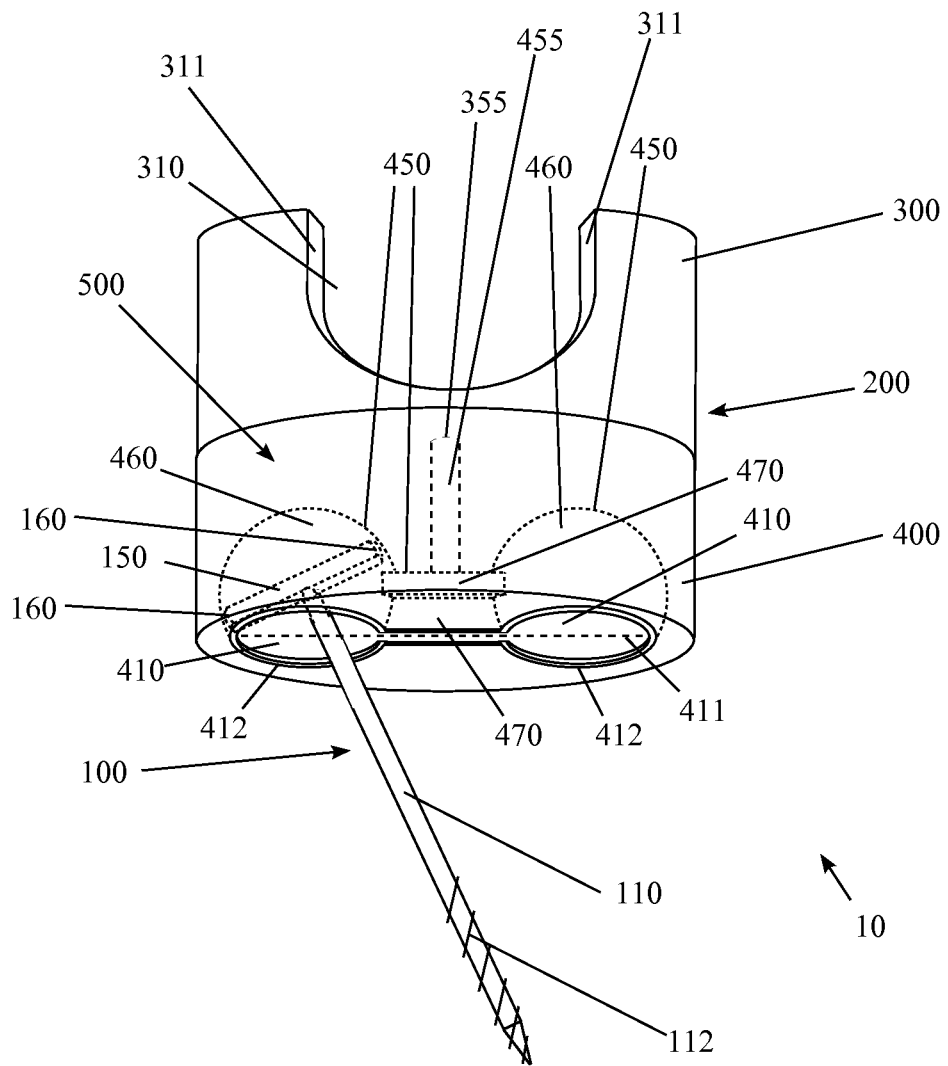
FIG. 5 is a perspective view showing the bottom of a bone fixation assembly with features of the invention, according to one exemplary embodiment, with a transparent view of the lower portion.

FIG. 5 is the same as FIG. 4, but with a transparent view of the lower portion 400. It shows tulip assembly 200 with upper portion 300 and lower portion 400. Also, the bone fixation device 100 is shown in angle with respect to the tulip assembly 200.

The transparent view of FIG. 5 shows an embodiment of a tulip assembly translation mechanism 500 inside tulip assembly 200 of the bone fixation assembly 10. This translation mechanism 500 comprises a head 150, a cavity 450, and an aperture 410 with an aperture length 411. The transparency reveals that the head 150 has distal ends 160. The bone fixation portion 110 has threads 112 and is extending away from head 150 and out of the cavity 450 through the aperture 410. The head is angled inside the cavity 450. The figure also shows two spherical contours 460 and a tunnel or channel 470 between them, all extending upwards from the aperture 410. Channel 470 is shaped or dimensioned to allow head 150 and bone fixation portion 110 to pass through it. The spherical contours 460 and the channel 470 describe the shape and space of the cavity 450. The head 150 is also shown to have a head length that is longer that the head width and the head height.

Figure 6:
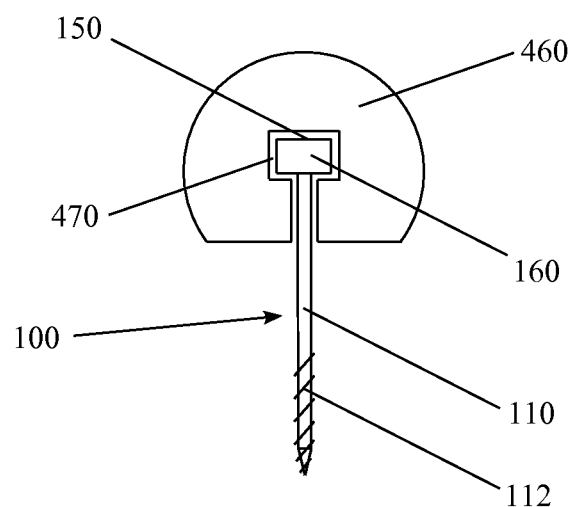
FIG. 6 is a side view of a spherical contour with a bone fixation device inside.

The spherical contours 460 are not necessarily completely spherical. Their bottoms are slit off by the aperture 410. Also, if there is a channel 470 linking to the spherical contour 460, the spherical contour 460 will provide open passage for the bone fixation device 100 into the channel 470, as shown in FIG. 6. Other embodiments may have different amounts of spherical contours and channels, with different sizes, shapes and in different directions not in straight lines (the aperture length may be curved).

The distal ends 160 are what reaches and touches the spherical contour 460. The head 150 will have distal ends 160 depending on its shape and design. If it is shaped as a sphere, it has no distal ends. If the head 150 is a beam with ball bearings on each end, the distal ends 160 are ball bearings. If the head 150 is shaped as a rectangular prism, with rectangular edges on all its sides, the distal ends will be each of the 4 corners on each of both ends of the prism. In FIG. 5, distal ends 160 are smoothed out to match the curvature of the spherical contour 460. Although the distal ends 160 are distanced from each other to reach the spherical contours 460, they are not necessarily touching each other all the time, as the head 150 may be moving between or placed in a channel 470 between spherical contours 460, in which case the distal ends would still be distanced to reach the spherical contours 460, but not actually reaching or touching them. This is shown explicitly in FIGS. 8A to 8C.

In order to avoid the whole bone fixation device 100 form being separated form the rest of the bone fixation assembly 10, a means for holding the bone fixation device 100 with the tulip assembly 200 has to be in place. One way to do this is to shape of the cavity such that the head or some other part of the bone fixation device cannot pass out of the cavity through the aperture and out of the tulip assembly. Another way is to have the aperture dimensioned to prevent the head or some other part of the bone fixation device from passing through the aperture (or, more broadly, to prevent the entire bone fixation device from passing through the aperture). The dimension of the aperture is defined by its size and shape. A too big aperture will just let the bone fixation device to fall off. A too small or tight aperture may cause the bone fixation device to not be able to angle with respect to the tulip assembly as much as it otherwise could. The shape of the aperture 410 should match the desired shape, size, direction and placement of the spherical contours, the channels, or any other shape or contour desired in the cavity. In FIGS. 4 and 5, a aperture wall or border 412 is shown. The aperture comprises this border or blocking element 412 as part of its shape or dimension, and it can be seen in FIG. 5 that this border 412 is blocking the continued shifting of the head 150 out of the cavity 450 through the aperture 410.

Alternatively, the spherical contours 460 could comprise a blocking element (equivalent to border 412) which could be placed inside the cavity 450 or at the meeting of the spherical contours 460 and the aperture 410; however, this may reduce the angling a little bit more. An equivalent structure would have a blocking means or blocking element within the cavity to stop the head or the whole bone fixation device from completely separating from the rest of the bone fixation assembly.

FIG. 5 also shows driving hole 355 leading to driving hole shaft 455. As explained in the explanation for FIG. 3 above, an appropriate driving tool would be inserted and pass through driving hole 355 and through driving hole shaft 455 to reach a head driving element (not shown) on head 150 through an entrance to the cavity (also not shown) when the head 150 is centered in the channel 470 in order to drive the bone fixation assembly 10 into a bone or tissue.

FIG. 6 is a side view of one spherical contour 460 with a bone fixation device 100 inside. The beginning of a channel 470 reveals the bone fixation device 100 inside the spherical contour 460. The bone fixation device 100 has a head 150 on the top, with a bone fixation portion 110 extending below with threads 112. Facing into the channel 470 is one of the distal ends 160, which is not touching the spherical contour 460. This figure shows how the channel has to match the shape of the head and of the bone fixation device; otherwise, there is no translation.

Figure 7:
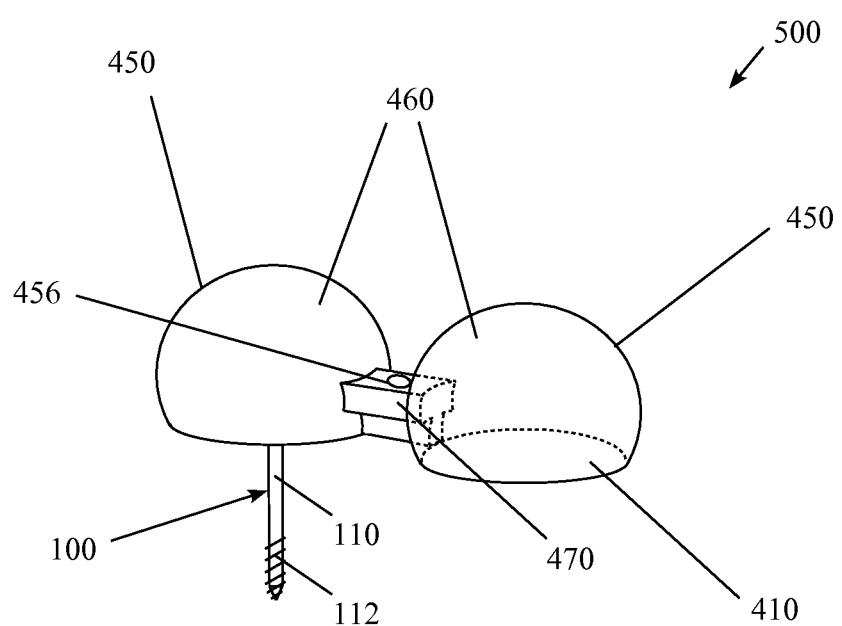
FIG. 7 is a perspective view of a tulip assembly translation mechanism, with a bone fixation device extending out from the left spherical contour, and with a transparent view of the right spherical contour.

FIG. 7 shows a perspective view of a tulip assembly translation mechanism 500, with a bone fixation portion 110 of a bone fixation device 100 extending out from the one of the spherical contours 460, and with a transparent view of another spherical contour 460. The transparent view reveals the aperture 410 below the spherical contour 460, and the entrance to and shape of the channel 470. The channel 470 is located between the spherical contours 460. On top of the channel 470 is the cavity driving hole or entrance 456 to the cavity 450 for the driving tool that passes through the driving hole shaft 455, as shown in FIG. 5 and explained above. Notice that aperture 410 does not have a blocking element 412, so the head (not shown) has to be maintained inside the cavity by other means (for example, by introducing obstacles or blocking means, or by making the bone fixation portion 110 broader so that it hits the aperture in a smaller angle and prevents the sliding of the head out through the aperture, or by making the aperture smaller to reduce the degrees reachable by the head, or by making the spherical contour 460 and the head and the aperture 410 all smaller, or by keeping the aperture size but making the spherical contour 460 and the head larger).

Figure 8A:
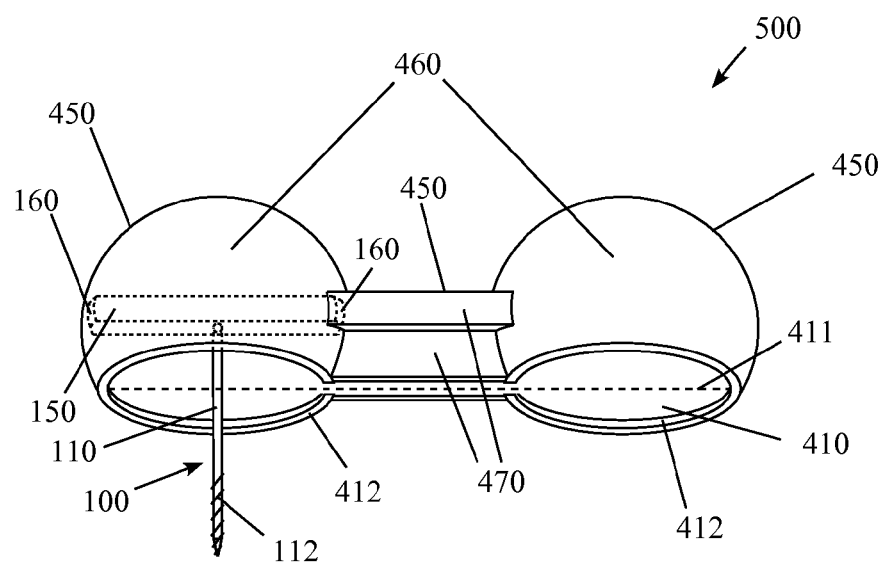
FIGS. 8A, 8B, and 8C are transparent perspective views of a tulip assembly translation mechanism showing the translation or movement of a bone fixation device.
Figure 8B:
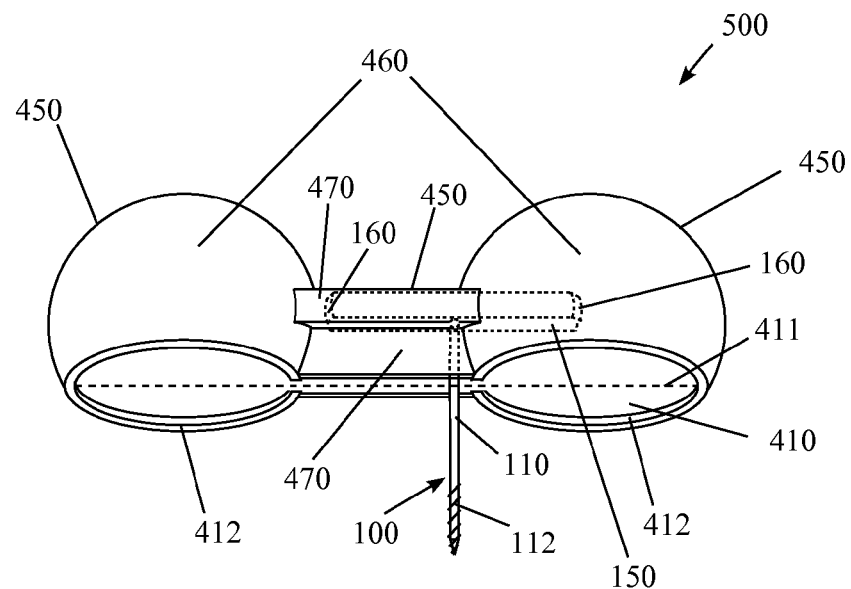
Figure 8C:
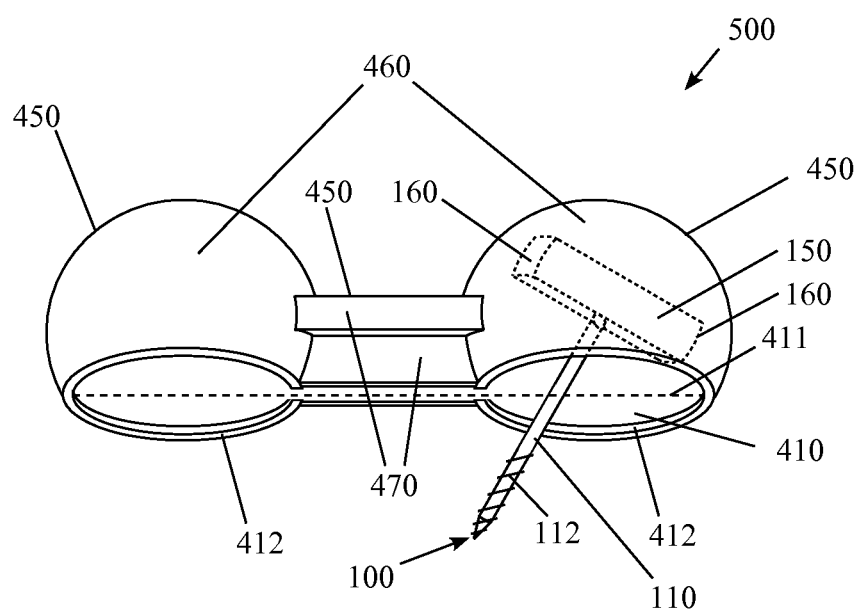

FIGS. 8A, 8B, and 8C are transparent perspective views of a tulip assembly translation mechanism 500 showing the translation or movement of a bone fixation device 100. The translation mechanism 500 shown is the same as the one in FIG. 5. The bone fixation device 100 is shown moving from the left spherical contour 460 to right spherical contour 460 through tunnel or channel 470 through FIGS. 8A to 8C. On FIG. 8C, the bone fixation device 100 is angling. FIGS. 8A, 8B, and 8C show that the head 150 may be moved in different angles with respect to the cavity 450 when the distal ends 160 are contiguous to one spherical contour 460 of the two spherical contours 460.

Figure 9A:
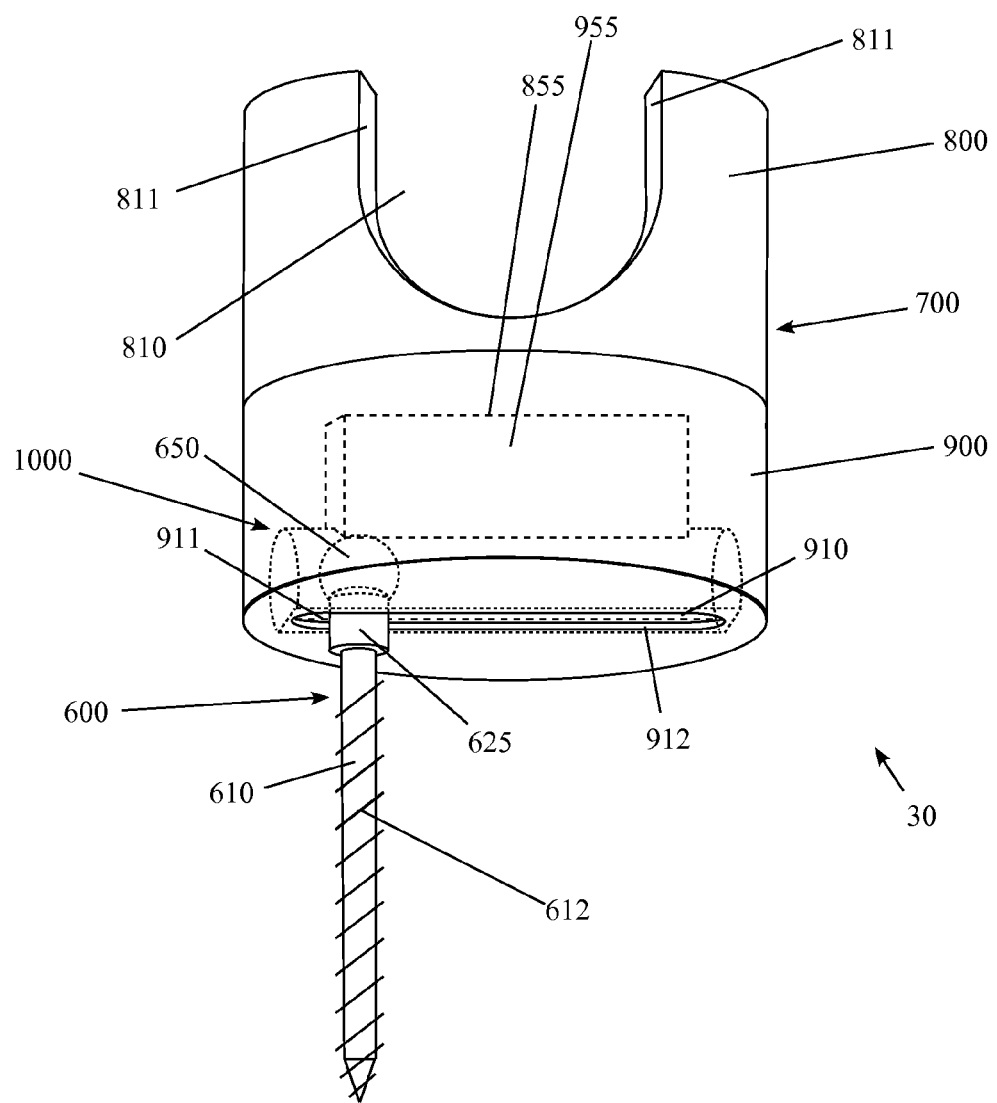
FIGS. 9A and 9B are perspective views showing the bottom of a bone fixation assembly with features of the invention, according to a second exemplary embodiment.
Figure 9B:
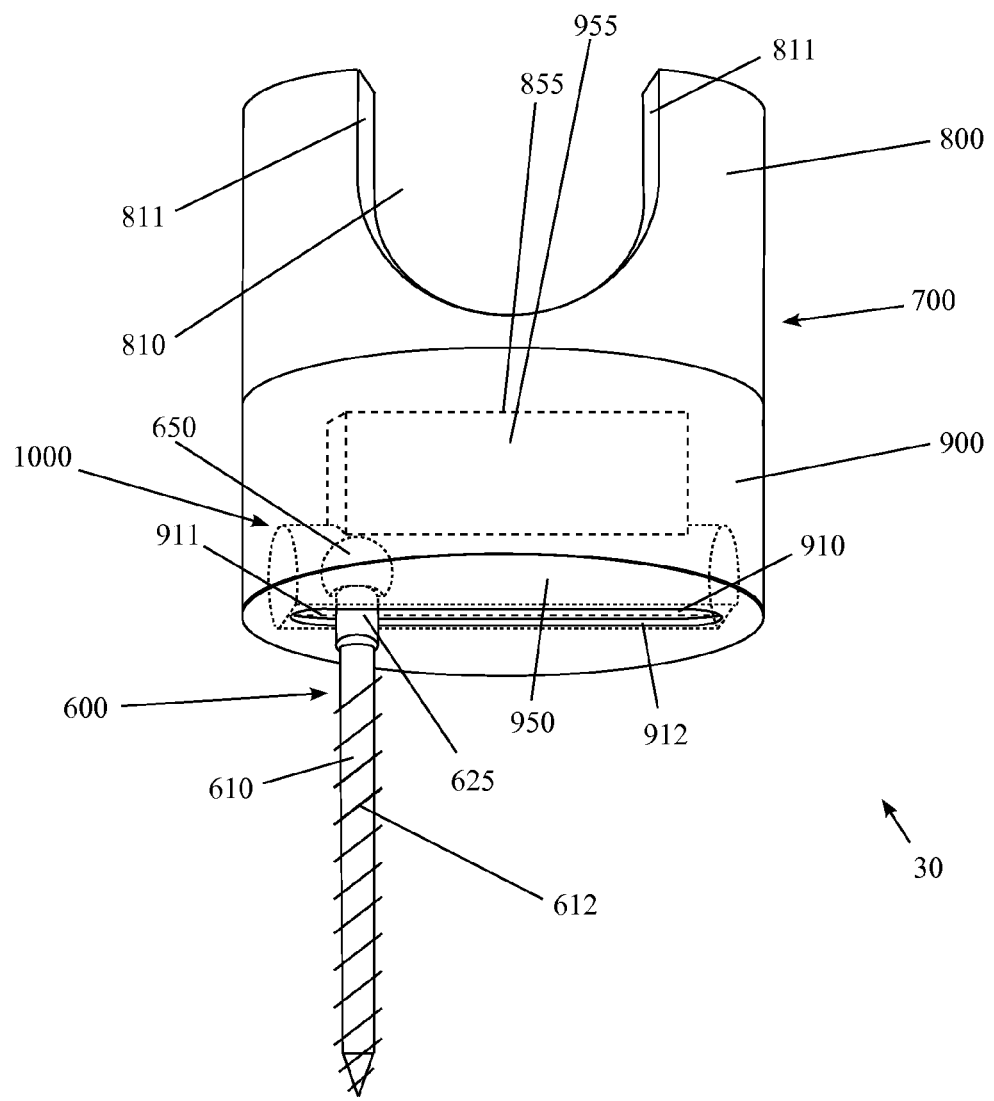

FIGS. 9A and 9B show a second exemplary embodiment featuring bone fixation assembly 30. The bone fixation assembly 30 has a bone fixation device 600 and a tulip assembly 700. The bone fixation device 600 comprises a bone fixation portion 610 and a head 650. The bone fixation portion 610 comprises threads 612 and a aperture engaging part or aperture engaging portion 625. Head 650 extends above aperture engaging portion 625.

Tulip assembly 700 comprises an upper portion 800 and a lower portion 900. Upper portion 800 extends upward from lower portion 900 and has a saddle 811 with the shape of the letter "U". Such shape creates a rod channel 810 to receive a rod. It also has locking element threads (not shown). The upper portion 800 is like the upper portion 300 of FIGS. 1 to 4, but with differences that will be more apparent and shown in FIG. 11.

Lower portion 900 is transparent to show a tulip assembly translation mechanism 1000 inside. The translation mechanism 1000 comprises a head 650, a cavity 950, and aperture 910 below the cavity 950. The aperture 910 comprises an aperture length 911 and an aperture wall or surface 912.

Above the cavity 950 is driving hole 955. An appropriate driving tool is inserted from the top through the upper portion 800 and through the driving slit 855 which is on the upper portion floor (not shown). The tool goes through the driving hole 955 and through the cavity entrance (not shown) to reach the bone fixation device 600. This will be shown with more detail on FIG. 11.

Although it does not necessarily have to be so, FIGS. 9A and 9B show an aperture 910 as straight. The aperture length 911 has no curvature. However, this is done for simplicity to show the important aspects of the invention.

Head 650 is shown to be spherical, making bone fixation device 600 a polyaxial screw. Other head shapes may have maintained the polyaxial nature of the bone fixation device 600. A simple example would be a head with an ellipsoid shape. Aperture engaging portion 625 is shown to have an elliptical cylinder shape. In FIGS. 9A and 9B, Aperture engaging portion 625 has a length that is equal or substantially equal to the width of aperture 910. FIG. 9A shows an aperture engaging portion that is not engaging the aperture: in the figure, the length of aperture engaging portion 625 has the same orientation as the aperture length 911, and there the bone fixation device 600 may be moved through the aperture length 911. In FIG. 9B, the aperture engaging part 625 is engaging the aperture 910: the length of aperture engaging portion 625 is perpendicular to the aperture length 911, and given that aperture engaging portion 625 has a length that is equal or substantially equal to the width of aperture 910, the aperture engaging portion 625 is locked by surface pressure with the surface 912 of the aperture 910. Notice that the locking of the aperture engaging portion is with respect to the aperture length: the bone fixation device 600 may be in any angle with respect to tulip assembly 700, and if the surface pressure between the aperture engaging part 625 and the surface 912 permits it, the angle between the bone fixation device 600 and the tulip assembly 700 may still be changed while the aperture engaging part 625 is still engaging the aperture 910 and locked in position in the aperture length 911. Other means for engaging the aperture 910 and configurations of the aperture 910, the aperture wall 912, and the aperture engaging portion 625 will also achieve similar results, as surface pressure is not the only means to lock the aperture engaging part 625 in position. For example, an aperture may be shaped with ridges that an aperture engaging part fits into and locks the aperture engaging part in position. Other complementary shapes between the aperture engaging part and the aperture may be designed to enable locking of the aperture engaging part in the aperture length.

Figure 10A:
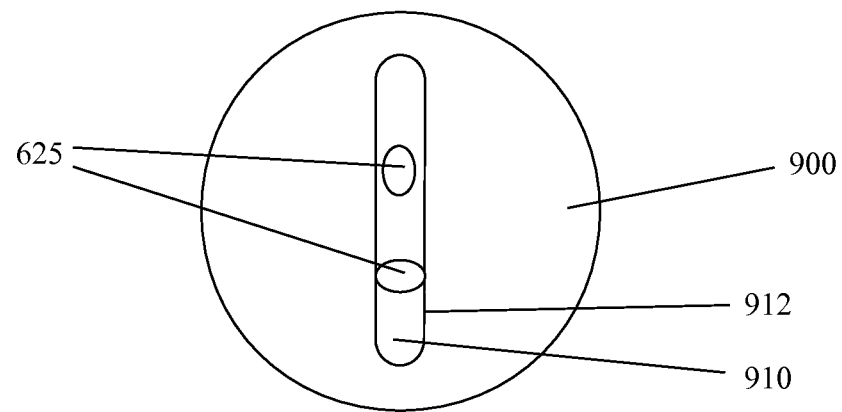
FIGS. 10A and 10B show a bottom view of a bone fixation assembly with features of the invention, according to the second exemplary embodiment.
Figure 10B:
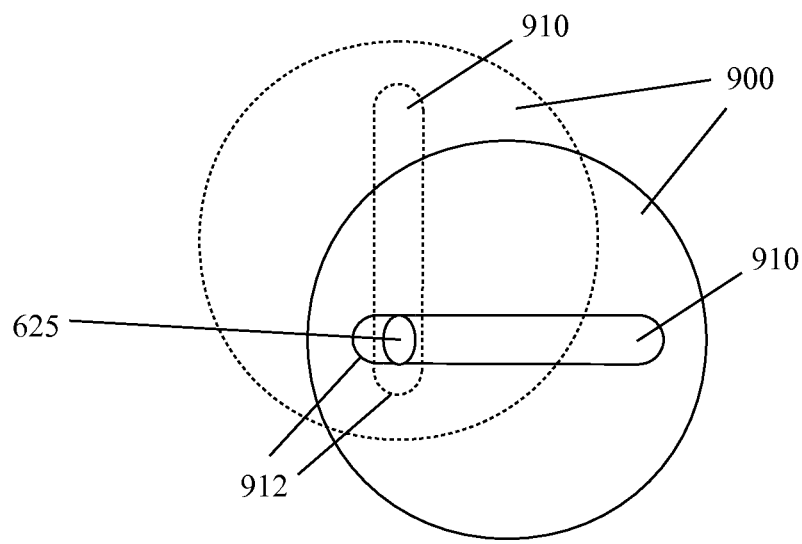

FIGS. 10A and 10B show a bottom view of lower portion 900 of the bone fixation assembly 30. FIG. 10A shows the aperture 910 and the aperture wall 912. The aperture engaging part 625 is shown twice, inside the aperture 910, while hiding the head and the rest of the bone fixation portion. The aperture engaging part 625 shown above, has its length oriented in the same direction as the aperture length 911 (not identified), while the aperture engaging portion 625 below is shown to engage the aperture and cause surface pressure with the aperture wall 912.

FIG. 10B is a bottom view example of the change between FIGS. 9A and 9B. An aperture engaging part 625 is shown not engaging an aperture 910 in the dotted lines, while it is engaging the aperture 910 while causing surface pressure on surface 912 on the solid line version of the lower portion 900. This figure makes it explicit that if the bone fixation portion 600 and its aperture engaging part 625 are going to be fixed with respect to a bone and not moved, the surgeon has to mind which is the desired final position of the tulip assembly, as movement through the aperture length will determine how far away from the center the tulip assembly will be, and the direction of the head may determine the locked position orientation of the aperture length (after all, the device does not have the be in locked position to be used as a tulip-translation enabled bone fixation assembly.) An alternative during implementation is to use a head driving tool, after the tulip assembly 700 is in the desired position and angle, to twist the bone fixation device 600 and the aperture engaging part 625 into lock position. This quick twist will generally result in minimal change or no significant damage in the bone structure of the patient and will be easy to execute by a surgeon.

Figure 11:
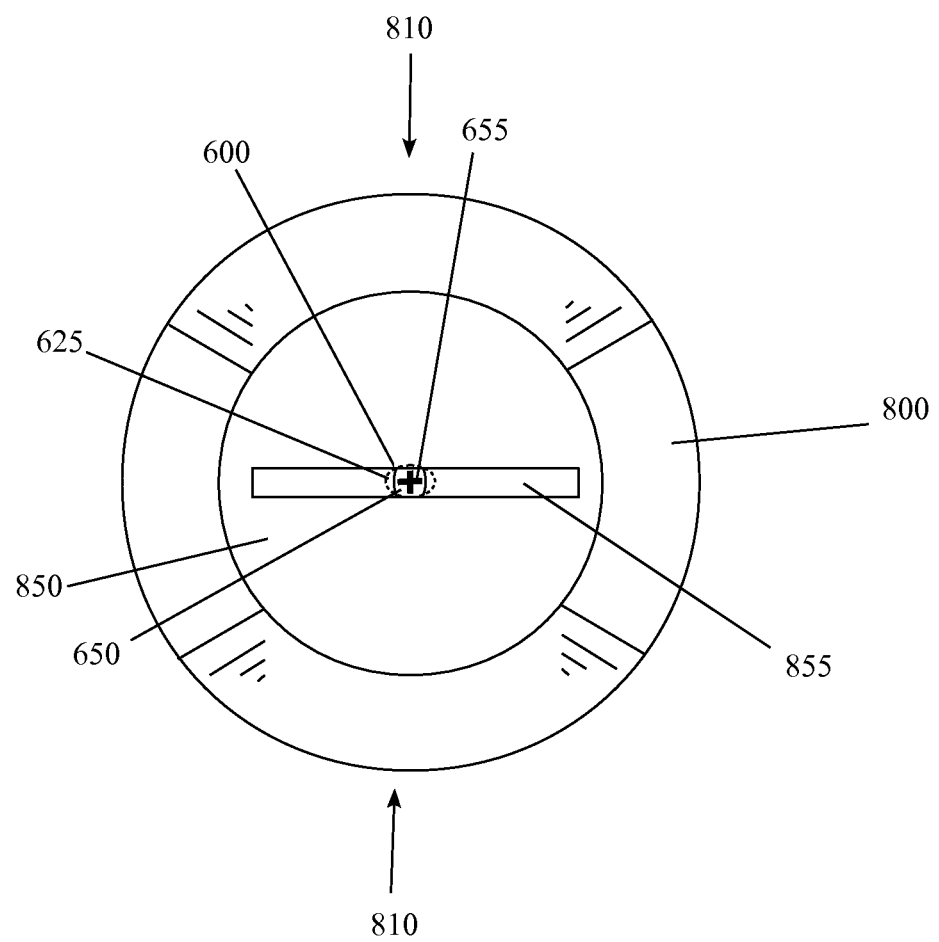
FIG. 11 shows a top view of a bone fixation assembly with features of the invention, according to the second exemplary embodiment.

FIG. 11 shows a top view of upper portion 800 of bone fixation assembly 30. Only upper portion 800 is seen of the tulip assembly 700. The figure shows the top of saddle 811 and shows the direction of rod channel 810. On the center of the upper portion floor 850 is a driving slit 855. Below the driving slit 855 is the driving hole 955 (not shown). Through driving slit 855 can be seen head 650 of the bone fixation device 600. On top of head 650 is a head driving element 655. The dashed line around the head 650 is the aperture engaging part 625. An appropriate driving tool is inserted through the upper portion 800 and goes into driving slit 855, through driving hole 955 (not shown), through the cavity entrance 956 (not shown), and grasps into the head driving element 655 to screw or place the bone fixation assembly 30 into a bone.

Figure 12:
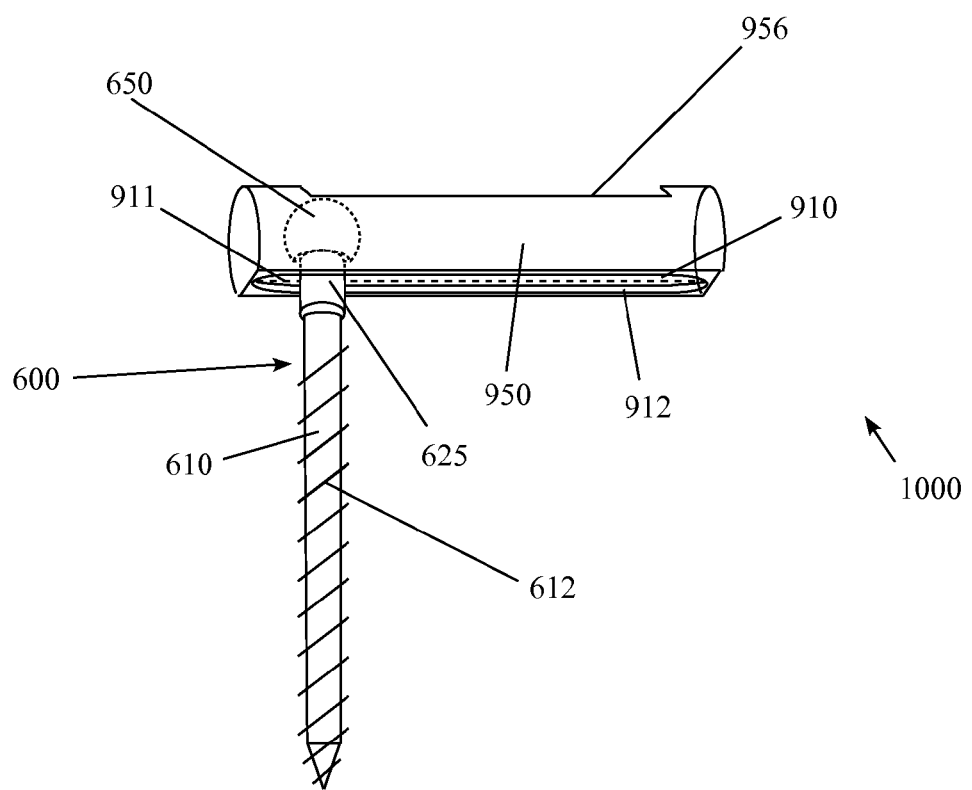
FIG. 12 is a perspective view of a second embodiment of a tulip assembly translation mechanism, with a bone fixation device extending out and with a transparent view of the cavity.

FIG. 12 shows tulip assembly translation mechanism 1000. The translation mechanism 1000 comprises the head 650, the cavity 950, and the aperture 910. The cavity 950 has a substantially cylindrical shape. Below the cavity is the aperture 910. The aperture 910 has an aperture length 911, an aperture surface 912, and the cavity 950 extends upward from the aperture 910, all like in FIGS. 9A and 9B. FIG. 12 also shows cavity entrance 956. Also like FIGS. 9A and 9B, head 950 is spherical, and below it extends the aperture engaging part 625. below aperture engaging part 625 extends the rest of bone fixation portion 610 with threads 612. Again, aperture engaging part 625 has an elliptic cylindrical shape.

Figure 13:
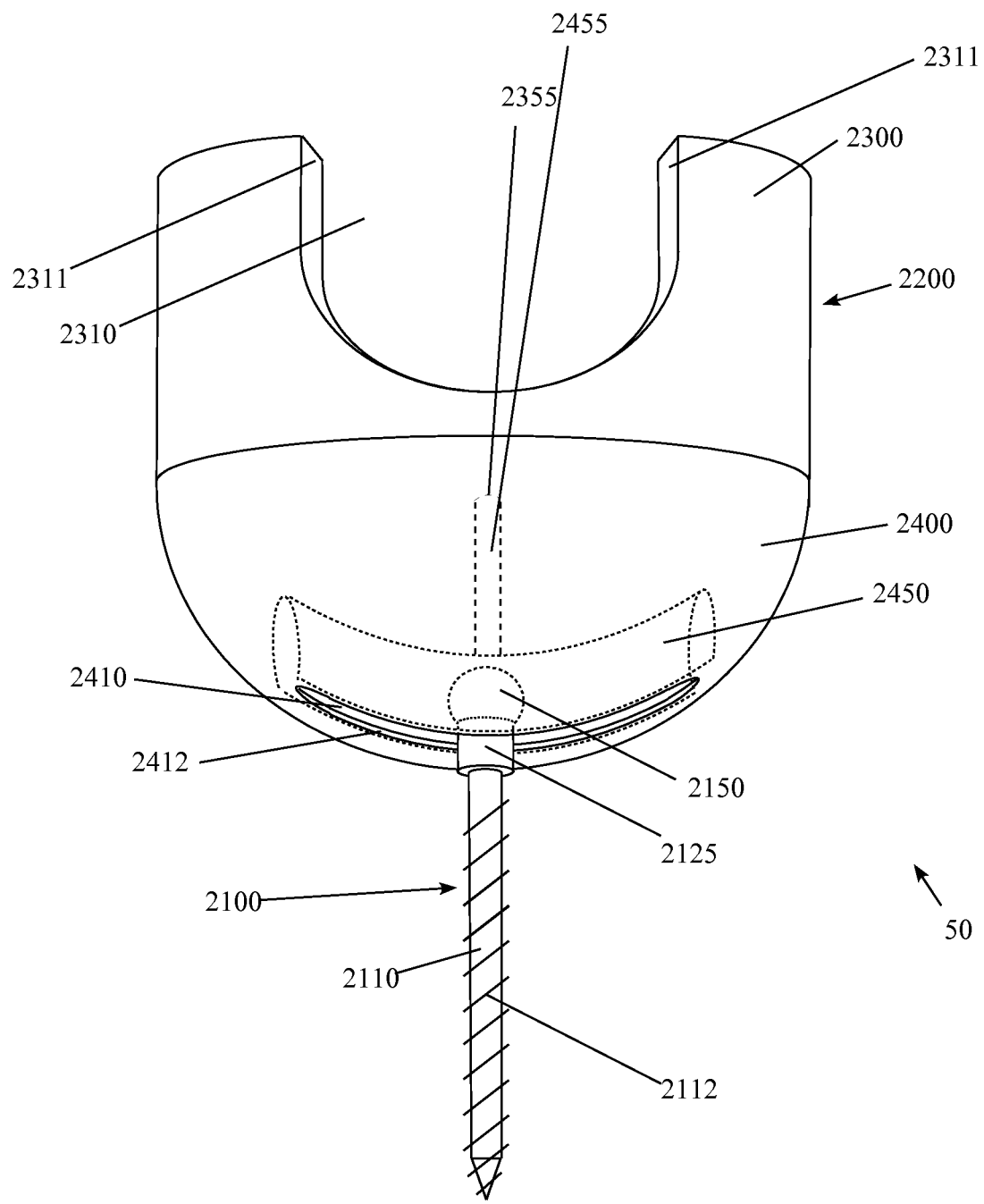
FIG. 13 is a perspective view of a third embodiment of a bone fixation assembly, with a transparent view of the lower portion.

FIG. 13 is another embodiment of the invention, featuring a bone fixation assembly 50. This FIG. 13 shows that it is possible to bend the previously shown embodiments, and have curved apertures and cavities. The bone fixation assembly 50 has a tulip assembly 2200 and a bone fixation device 2100. Tulip assembly 2200 has upper portion 2300 and lower portion 2400. Upper portion 2300 extends above upwards from lower portion 2400, and is structured to receive a rod. Upper portion 2300 has a "U" shaped saddle 2311 made by two concavities on the wall of upper portion 2300, which creates a rod channel 2310 for receiving a rod. In short, the upper portion 2300 is equal to and the same as the upper portion 300 of the bone fixation assembly 10 shown in FIGS. 1 through 5.

The bone fixation device 2100 has a polyaxial ellipsoid shaped head 2150 and a bone fixation portion 2110. The ellipsoid shape is polyaxial due to the space provided by the cavity 2450. Extending below the head 2150 is the aperture engaging portion 2125, continued by the rest of the bone fixation portion 2110. The bone fixation portion 2110 also comprises threads 2112 and the aperture engaging portion 2125.

The head 2150 is inside the curved cavity 2450. Above cavity 2450 is the cavity entrance (not shown) for allowing driving tools to reach the driving element (not shown) on the head 2150. The driving tool reaches through driving hole 2355 and down through driving shaft 2455. Driving shaft 2455 is on top of the cavity entrance, and the driving hole 2355 on top of the driving shaft. Below cavity 2450, at the bottom of lower portion 2400, is aperture 2410, which comprises an aperture length (not identified) and an aperture wall 2412. The aperture 2410 follows the concavity-like curve and shape of the outer surface of lower portion 2400. The aperture engaging part 2412 can engage the aperture 2410 in the same manner described above for the description of FIGS. 9A to 12 for aperture engaging part 625.

Figure 14:
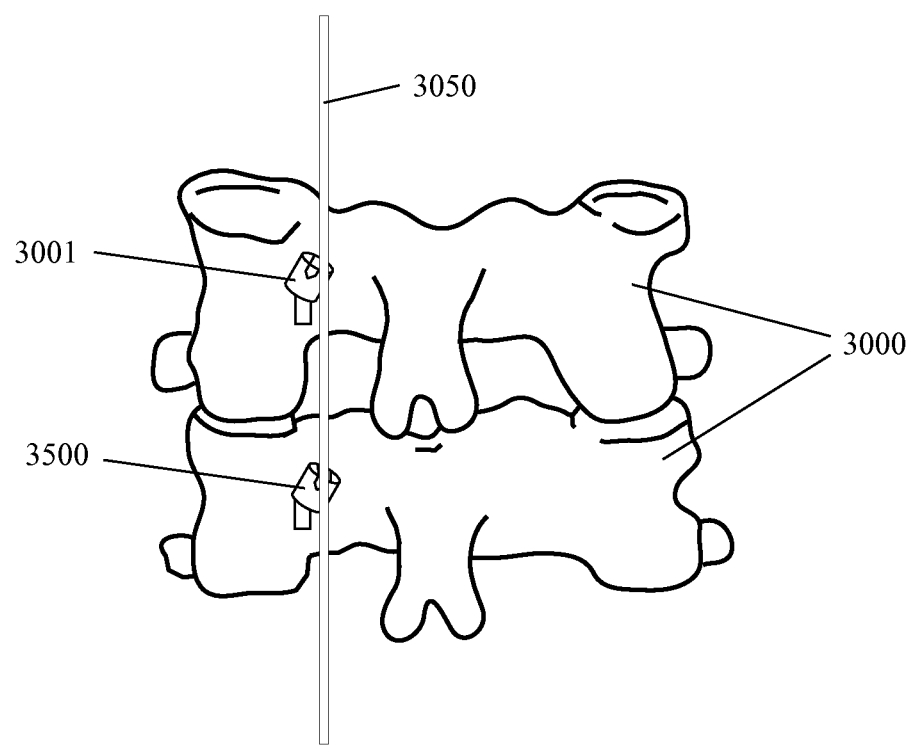
FIG. 14 is a posterior view of two cervical bones with an implementation of an embodiment of a bone fixation assembly with features of the invention.

FIG. 14 presents a posterior view of two cervical bones 3000 with an implementation of the embodiment of a bone fixation assembly with features of the invention. The cervical bone 3000 on top has a bone fixation assembly 3001 that does not incorporate features of the present invention; therefore, it has no means to translate the tulip assembly medially towards the rod 3050. Reaching the rod 3050 with bone fixation assembly 3001 will require one or a combination of additional parts, plates, bending the rod 3050, or a substitution of the bone fixation assembly 3001 with another component or surgical screw. In any case, it will require more surgical time and effort from the surgeon.

The cervical bone 3000 below has a bone fixation assembly 3500 that incorporates features of the present invention; therefore, although its bone fixation portion was installed at the same distance away from the rod 3050, it has means to translate the tulip assembly medially towards the rod 3050, and does reach the rod 3050. Sometimes the benefit of a few millimeters in tulip translation saves time for the surgeon. In other scenarios, the translation will mean that the rod being used in surgery will not have to be bent as much. Generally, the material used to manufacture the rod with is titanium, which creates memory as it is bent; bending it back or bending again the rod may debilitate its structure. Often, surgeons have to discard a rod during surgery due to the possible mechanical failure of the rod. So the less bending of the rod will result in better mechanical performance, less surgical time, and less costs in materials.

Other embodiments are within the scope of the following claims. The embodiments of the invention may be made of any solid material, but generally these materials should be appropriate for placement in the human body. Usually, the bone fixation assembly will be made of metal, plastic, ceramic, bone, polymers, composites, absorbable material, biocompatible material, alloy, or combinations thereof. MRI (magnetic resonance imaging) compatible, titanium made embodiments are preferred.

While the invention has been described as having certain preferred designs, it is understood that many changes, modifications, variations and other uses and applications of the subject invention will, however, become apparent to those skilled in the art without materially departing from the novel teachings and advantages of this invention after considering this specification together with the accompanying drawings. Accordingly, all such changes, modifications, variations and other uses and applications which do not depart from the spirit and scope of the invention are deemed to be covered by this invention as defined in the following claims and their legal equivalents. In the claims, means-plus-function clauses, if any, are intended to cover the structures described herein as performing the recited function and not only structural equivalents but also equivalent structures.

All of the patents, patent applications, and publications recited herein, and in the Declaration attached hereto, if any, are hereby incorporated by reference as if set forth in their entirety herein. All, or substantially all, the components disclosed in such patents may be used in the embodiments of the present invention, as well as equivalents thereof. The details in the patents, patent applications, and publications incorporated by reference herein may be considered to be incorporable at applicant's option, into the claims during prosecution as further limitations in the claims to patentable distinguish any amended claims from any applied prior art.

I claim:

1. A bone fixation assembly comprising:
   (a) a bone fixation device comprising
      a bone fixation portion and a head, said bone fixation portion extending away from said head; and (b) a tulip assembly comprising
an upper portion and a lower portion, said upper portion extending upward from said lower portion and structured to receive a rod,
and said lower portion comprising
a cavity within said lower portion, and
an aperture to the cavity, said aperture located below said cavity, and said head being inside said cavity with said bone fixation portion extending out through said aperture,
said aperture comprising an aperture length,
said aperture dimensioned to prevent the entire bone fixation device from passing through said aperture and to allow said tulip assembly to slide on said bone fixation device through said aperture length;
whereby when said bone fixation device is fixed to a bone said tulip assembly may be moved with respect to said bone through the aperture length to reach the rod to be fitted in said tulip assembly.

2. The bone fixation assembly of claim 1, wherein said bone fixation device comprises a polyaxial screw, said polyaxial screw comprising said head and said bone fixation portion.

3. The bone fixation assembly of claim 1, wherein said head has a head length, a head height, and a head width, in which said head length is longer than said head height and longer than said head width.

4. The bone fixation assembly of claim 1, wherein said cavity further comprises an at least one spherical contour, each of said at least one spherical contour extending upwards from said aperture.

5. The bone fixation assembly of claim 4, wherein said head further comprises distal ends, wherein said distal ends reach said at least one spherical contour, whereby said tulip assembly may be moved in different angles with respect to said head when said distal ends are contiguous to said at least one spherical contour.

6. The bone fixation assembly of claim 1, wherein said cavity further comprises
(a) an at least two spherical contours, each of said at least two spherical contours extending upwards from said aperture, and
(b) an at least one channel, each of said at least one channel extending between two of said at least two spherical contours while also extending upwards form said aperture through said aperture length, and dimensioned to allow said head to pass through said at least one channel.

7. The bone fixation assembly of claim 6, wherein said head further comprises distal ends, with said distal ends distanced to reach inside each one of said at least two spherical contours.

8. A bone fixation assembly comprising:
(a) a bone fixation device comprising
a head, and
a bone fixation portion, said bone fixation portion comprising an aperture engaging portion, said bone fixation portion extending away from said head; and
(b) a tulip assembly comprising
an upper portion and a lower portion, said upper portion extending upward from said lower portion and structured to receive a rod, said lower portion comprising a cavity within said lower portion, and an aperture to the cavity, said aperture located below said cavity and said aperture comprising an aperture length, said aperture engaging portion structured to lock in position in said aperture length in at least in one orientation of said aperture engaging portion with respect to said aperture; said aperture dimensioned to prevent the entire bone fixation device from passing through said aperture and to allow said tulip assembly to slide on said bone fixation device through said aperture length when said aperture engaging portion is not locked in position in said aperture length; whereby when said bone fixation device is fixed to a bone and said aperture engaging portion is not locked in position with respect to said aperture length, then said tulip assembly may be moved to reach the rod to be fitted in said tulip assembly and then said tulip assembly may be locked in position with respect to said aperture length.

9. The bone fixation assembly of claim 8, wherein said bone fixation device comprises a polyaxial screw, said polyaxial screw comprising said head and said bone fixation portion.

10. The bone fixation assembly of claim 8, wherein said aperture engaging portion has an elliptic cylindrical shape.

11. A tulip assembly translation mechanism of a bone fixation assembly, said mechanism comprising:
(a) a head of a bone fixation device, wherein said head has a head length, a head height, and a head width, in which said head length is longer than said head height and longer than said head width;
(b) a cavity of a tulip assembly, said head located inside said cavity; and
(c) an aperture to said cavity, said aperture comprising an aperture length and located below said cavity; said aperture dimensioned to prevent said head from passing through said aperture, and said cavity dimensioned to allow said head to move through said cavity by said aperture length.

12. The mechanism of claim 11, said mechanism further comprising an aperture engaging part, said aperture engaging part extending below said head from inside the cavity out through said aperture and structured to lock in position in said aperture length in at least one orientation of said aperture engaging part with respect to said aperture.

13. The mechanism of claim 12, wherein said aperture engaging part locks movement through said aperture length with said aperture through surface pressure between said aperture engaging part and said aperture in at least one orientation of said aperture engaging part with respect to said aperture.

14. The mechanism of claim 12, wherein said aperture engaging part has an elliptic cylindrical shape.

15. The mechanism of claim 11, wherein said cavity further comprises an at least one spherical contour, each of said at least one spherical contour extending upwards from said aperture.

16. The mechanism of claim 15, wherein said head has a head length, a head height, and a head width, in which said head length is longer than said head height and longer than said head width.

17. The mechanism of claim 16, wherein said head further comprises distal ends, wherein said distal ends reach said at least one spherical contour.

18. The mechanism of claim 11, wherein said cavity further comprises
(a) an at least two spherical contours, each one of said at least two spherical contours extending upwards from said aperture, and
(b) an at least one channel, each of said at least one channel extending between two of said at least two spherical contours while also extending upwards form said aperture through said aperture length, and dimensioned to allow said head to pass through said at least one channel.

19. The mechanism of claim 18, wherein said head further comprises distal ends, with said distal ends distanced to reach each one spherical contour of said at least two spherical contours, whereby said head may be moved in different angles with respect to said cavity when said distal ends are contiguous to one spherical contour of said at least two spherical contours.

* * * * *